(12) United States Patent
Gershaw

(10) Patent No.: US 8,106,569 B2
(45) Date of Patent: Jan. 31, 2012

(54) LED RETROFIT FOR MINIATURE BULBS

(75) Inventor: David Gershaw, Danvers, MA (US)

(73) Assignee: RemPhos Technologies LLC, Danvers, MA (US)

( * ) Notice: Subject to any disclaimer, the term of this patent is extended or adjusted under 35 U.S.C. 154(b) by 0 days.

(21) Appl. No.: 12/778,264

(22) Filed: May 12, 2010

(65) Prior Publication Data

US 2010/0314986 A1 Dec. 16, 2010

Related U.S. Application Data

(60) Provisional application No. 61/177,487, filed on May 12, 2009.

(51) Int. Cl.
*H01J 7/24* (2006.01)
*F21V 29/00* (2006.01)
*A61B 1/06* (2006.01)

(52) U.S. Cl. .......... 313/46; 313/512; 600/249; 362/264; 362/294; 362/345; 362/373

(58) Field of Classification Search ................. None
See application file for complete search history.

(56) References Cited

U.S. PATENT DOCUMENTS

| | | | |
|---|---|---|---|
| 3,698,387 A | 10/1972 | Moore et al. | |
| 5,998,925 A | 12/1999 | Shimizu et al. | |
| 6,069,440 A | 5/2000 | Shimizu et al. | |
| 7,276,025 B2 | 10/2007 | Roberts et al. | |
| 7,458,934 B2 | 12/2008 | Roberts et al. | |
| 7,491,000 B2 * | 2/2009 | Takehashi et al. | 385/92 |
| 2004/0079957 A1 | 4/2004 | Andrews et al. | |
| 2004/0186352 A1 | 9/2004 | Roberts et al. | |
| 2006/0024638 A1 | 2/2006 | Rosenblood et al. | |
| 2007/0010157 A1 * | 1/2007 | Sorg | 445/25 |
| 2008/0093962 A1 * | 4/2008 | Kim et al. | 313/46 |
| 2008/0273329 A1 | 11/2008 | Belek | |
| 2009/0323346 A1 * | 12/2009 | Chang | 362/294 |
| 2010/0171403 A1 * | 7/2010 | Yang et al. | 313/46 |

FOREIGN PATENT DOCUMENTS

| | | |
|---|---|---|
| JP | 2005251588 A | 9/2005 |
| JP | 2008505454 T | 2/2008 |

OTHER PUBLICATIONS

International Search Report and Written Opinion for application No. PCT/US2010/034469 mailed Dec. 27, 2010, 11 pages.

* cited by examiner

*Primary Examiner* — Ashok Patel
(74) *Attorney, Agent, or Firm* — Nutter McClennen & Fish LLP

(57) ABSTRACT

Methods and devices are provided for an improved light source. In one exemplary embodiment a light source includes a heat sink, a LED die, and a phosphor dome. A conductive material can be disposed in the heat sink, the LED die can be mounted to a top portion of the conductive material such that the LED die is in electrical contact with the heat sink, and the phosphor dome can be coupled to a top face of the heat sink. In another embodiment, a light source includes a heat sink, a sleeve, a LED package, and an optic. A conductive material can be disposed in the heat sink, the sleeve can be disposed around at least a portion of the heat sink and the conductive material, the LED package can be mounted above the conductive material, and the optic can be located above the LED package and coupled to the sleeve. The light sources disclosed herein can be used to replace existing miniature bulbs in a number of different devices, including medical devices such as otoscopes.

19 Claims, 15 Drawing Sheets

LED RETROFIT FOR MINIATURE BULBS

RELATED APPLICATIONS

The present invention claims priority to U.S. Provisional Patent Application Ser. No. 61/177,487, "LED Retrofit Otoscope/Opthalmoscope Lamp" and filed on May 12, 2009, the contents of which is hereby incorporated by reference in its entirety.

FIELD

This invention relates to many different fields which require a miniature light source in order to illuminate a desired instrument, apparatus, or device. More particularly this invention can be used in such industries as automotive (replacing traditional bulbs used to illuminate the dashboard, interior lighting, or exterior lighting), home or industrial appliances (replacing traditional bulbs used to illuminate display panels), and aircraft (replacing traditional bulbs used to illuminate display panels). While the design and components of the LED retrofit bulb described in this invention can be used in many different products, the specific product that will be shown as an example of a retrofit application in this invention is a medical instrument called an otoscope or opthalmoscope.

BACKGROUND

A lamp is put into a fixture to produce light. Miniature bulbs or lamps are by definition generally small in size and used, for example, for task or indicator lighting. The bulb described here is one for an otoscope or opthalmoscope.

An otoscope is an instrument used in the medical field to examine the external ear, the eardrum, and, through the eardrum, the ossicles of the middle ear. An opthalmoscope is a device used in the medical field to examine the eye. Both units can share the same basic concepts as follows. The scope can consist of a light and/or a magnifying lens. A scope can have a gripping body and a top attachment to shine light into a patient's ear or eye. The top attachment can be connected to a top end of the gripping body, and in some versions a viewing port can be connected to the top end of the gripping body, which itself can contain a battery compartment, to provide a line of sight through the ear speculum. A scope can also include a light source that is directed through the ear speculum. The disclosures of the present invention are directed in particular to this light source, as well as light sources used in many other industries, tools, instruments, and appliances. The majority of the above features are described, for example, in U.S. Pat. No. 3,698,387 to Moore et al., and as further illustrated in FIG. 1, which is a figure from U.S. Pat. No. 3,698,387 to Moore et al., the contents of which is incorporated by reference in its entirety.

Instruments, such as the devices described above, require inefficient large light sources such as incandescent, halogen, or tungsten. They require such large light sources because their collection and delivery of light design is inefficient. These large light sources use a great amount of electrical power that drains the small battery in these small devices quickly. Typically the traditional bulbs used in these applications have light illuminated in a very specific (usually omni-directional) manner, which is difficult to focus into a tight beam.

The light source used in the Welch-Allyn otoscope, for example, consists of a tungsten filament miniature lamp mounted on top of a removable hollow cylindrical metal piece as shown in FIG. 2. This lamp is powered by a rechargeable battery incased within the gripping body of the scope. The lamp makes electrical contact to the battery at the base of the cylindrical metal through an electrical insulated metal rod (anode) and through the outer metal cylinder (cathode). The lamp is turned on-off with the scope's switch that makes electrical contact at the outer wall of the metal hollow cylinder of the lamp. The lamp intensity is also dimmable via a resistor built into the switch. Some of the drawbacks of halogen bulbs are that they burn very hot and eagerly consume battery power, which causes the need to frequently recharge the lamps. They are also very fragile and easily damaged.

An alternative of this light source, as discovered as part of the present invention, is an LED light source as described in the present invention. One advantage of the present LED light source over halogen (incandescent) light sources is that the LED bulb contains no fragile filament that can be easily damaged and/or burned out over time. The LED light source of the present invention lasts more than 50,000 hours, essentially forever, and will not be damaged by rough handling, dropping, or sudden movement.

While at least one LED otoscope exists, it has a number of shortcomings. One embodiment of a LED otoscope is described in United States Patent Application Publication No. 2004/0186352 by Roberts et al., and as further illustrated in FIG. 3, which is a figure from United States Patent Application Publication No. 2004/0186352 by Roberts et al., the contents of which is incorporated by reference in its entirety. A major disadvantage to the LED otoscope described by Roberts is the resistance within the medical industry to change their existing devices. For example, Welch-Allyn is a trusted name in medical lighting instruments. The majority of medical personnel and facilities use Welch-Allyn devices which they have owned for many years. The device is trusted and therefore the medical personnel or facility has no desire to switch to a completely new device where the reliability is greatly unknown. The disclosures of the present invention allow for the light sources of the present invention to easily replace existing light sources, thereby allowing for easy retrofitting.

When an LED is going to be used in an application which has restrained physical space, thermal management is extremely important. A LED should be mounted to a heat sink with sufficient ability to pull heat away from the LED die without it reaching critical maximum temperatures. Most prior heat sinks require the use of wires, plastic, or other materials in order to electrically insulate the anode and cathode of the LED while connecting the anode and cathode to the power source. Any prior heat sink would suffer thermally from the use of materials which are not good thermal conductors.

SUMMARY

It is a primary object of the present invention to overcome all of the above-noted deficiencies of the prior art.

It is another primary object of the present invention to create a retrofit LED bulb that is a direct plug and play. A direct plug and play retrofit can be described as an installation where the operator removes the original bulb and replaces it with an LED bulb, and no additional wiring, electronics, or mechanical modifications are needed. There is believed to be a very large market where a retrofit LED bulb will be desirable because new and costly equipment will not need to be purchased.

In addition, prior art heat sinks are not thermally efficient enough to extract the heat from high power LED dies or packages. Newer, high power (1+ Watt) LEDs need a large enough heat sink so that the temperature at the junction of the die does not rise beyond the manufacturer's specified maximum junction temperature which is typically in the range of approximately 100° C. to approximately 130° C. A diagram of junction temperature (denoted as $T_j$) can be seen in FIG. 4.

For the above reasons it is therefore another primary object of the present invention that this LED retrofit invention be designed to fully optimize the existing otoscope's current optical system to the highest efficiency possible without requiring any modifications whatsoever. It was discovered by way of the present invention that the heat sink design of the present invention is one that takes full advantage of the otoscope's metal construction. This metal construction of the otoscope provides additional thermal extraction from the LED retrofit bulb and can keep the junction temperature below critical values.

Therefore, and according to a preferred aspect of the invention, there is disclosed a LED retrofit lamp for use in any miniature retrofit application, said lamp comprising:

an aluminum outer body;

an aluminum inner rod or rods;

a polycrystalline alumina tube or tubes or anodization around the aluminum inner rod(s) that acts as a thermal conductor but electrical insulator;

at least one white LED package or blue LED die with accompanying remote phosphor white light conversion for high color rendering index (CRI) and correct color temperature (CCT); and an optic that is designed for each application to efficiently extract the light from the white LED package or blue LED die with accompanying remote phosphor conversion. This optic could be in the form of many different shapes such as spherical, convex, concave, etc. Additionally, some applications may require no lens at all.

According to yet another preferred aspect of the present invention, there is disclosed a "LED retrofit lamp for Welch-Allyn otoscope" designed specifically for use inside a Welch-Allyn otoscope. The lamp can include all of the above aspects and features of the LED retrofit lamp, and additionally can include:

an aluminum outer body that can interface directly with the metal body allocated for the tungsten traditional bulb. By interfacing (and touching) the metal body of the otoscope, the LED lamp can use the metal body as an electrical contact. Additionally, it can use the metal body as a thermal contact point to extract heat away from the LED.

a single aluminum inner rod that can interface directly with the electrical pin of the otoscope to provide yet another thermal and electrical contact point; and a specific optic, which is described in further detail below.

In one exemplary embodiment of a light source in accordance with the present invention, the light source includes a heat sink having a conductive material disposed therein, a LED die, and a phosphor dome. The LED die can be mounted to a top portion of the conductive material of the heat sink. The LED die can be in electrical contact with the heat sink. The phosphor dome can be coupled to a top face of the heat sink. In one embodiment the conductive material is centrally disposed in the heat sink. The conductive material can include an electrically conductive rod that is disposed in at least a portion of the heat sink. In one embodiment an outer tube can be disposed around the electrically conductive rod of the conductive material. In one embodiment a color rendering index of the light source can be approximately greater than or equal to about 85. In another embodiment a color temperature can be approximately in the range of about 2700 K to about 3200 K. The heat sink can include one or more radiating fins. The heat sink can also include a polymer. The light source can also include a wire bond that is configured to create electrical contact between the LED die and the heat sink. Further, the light source can include silicone that can be disposed on at least a portion of at least one of the heat sink, the LED die, and the phosphor dome. In one exemplary embodiment a life expectancy of the light source can be approximately 50,000 hours.

In another exemplary embodiment of a light source in accordance with the present invention, the light source can include a heat sink having a conductive material disposed therein, a sleeve disposed around at least a portion of the heat sink and the conductive material, a LED package, and an optic. The LED package can be mounted above the conductive material, and the optic can be located above the LED package and coupled to the sleeve. In one embodiment the conductive material is centrally disposed in the heat sink. The conductive material can include an electrically conductive rod that is disposed in at least a portion of the heat sink. In one embodiment an outer tube can be disposed around the electrically conductive rod of the conductive material. In one embodiment a color rendering index of the light source can be approximately greater than or equal to about 85. In another embodiment a color temperature can be approximately in the range of about 2700 K to about 3200 K. The heat sink can include one or more radiating fins. The heat sink can also include a polymer. The light source can also include a spacer that is disposed between the LED package and the conductive material. In another embodiment the light source can include an optically clear substance that is located in a space surrounding the LED package. In one embodiment the LED package includes a blue chip, an on-chip phosphor conversion layer, and a ceramic substrate.

It is an object of the invention to provide an improved light source that has an increased lifetime of approximately 50,000 hours.

It is an object of the invention to provide an improved light source that has less energy consumption compared to traditional bulbs.

It is an object of the invention to provide an improved light source for which no fragile filament can be easily damaged or burned out over time.

It is an object of the invention to provide an improved light source that has a CRI and CCT that can match the requirements of an existing bulb being replaced.

It is an object of the invention to provide an improved light source that has equal or greater lumen output compared to the existing bulb being replaced.

It is an object of the invention to provide an improved light source that is a "green" environmentally friendly product.

These and other objects, features, and advantages will become readily apparent from the following Detailed Description which should be read in conjunction with the accompanying drawings.

BRIEF DESCRIPTION OF DRAWINGS

This invention will be more fully understood from the following detailed description taken in conjunction with the accompanying drawings, in which:

FIG. 11A is a partial, top view of the LED retrofit source of FIG. 10 illustrating a bottom portion of the white LED package;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention relates to devices in which a LED light source can be retrofitted, and methods of replacing current light sources with a LED light source as described herein. Light sources that can be replaced include existing miniature light bulbs. While the present description and figures primarily discuss the inventive light sources as being used in conjunction with an otoscope, a person skilled in the art will recognize that the inventive light sources disclosed herein, and methods related to the same, can be used in a variety of different instruments and tools across any number of industries. By way of non-limiting example, the inventive light sources, and methods related to the same, can be incorporated in other medical instruments and tools, such as diagnostic devices, ophthalmoscopes, anoscopes, vaginoscopes, and the like. By way of further non-limiting example, other industries in which the inventive light sources, and methods related to the same, can be used include household, business, and construction appliances, tools, and instruments, the automotive industry, such as for illuminating dashboards and for other interior and exterior lights, the aircraft industry, such as for panel illumination, the computer industry, the electronics industry, and any number of other industries in which miniature bulbs can be used as light sources. A person skilled in the art will further recognize that although the devices and methods discussed herein are primarily discussed with respect to retrofitting an existing device, the disclosed devices and methods can also be used in conjunction with manufacturing new devices and systems in any number of industries.

In the following description, well-known functions or constructions are not described in detail to avoid obscuring the invention in unnecessary detail.

One embodiment of a LED lamp emitting white light for the replacement of tungsten-halogen lamps in otoscopes is shown in FIGS. 5-8. This embodiment uses the concept of a remote phosphor conversion layer being disposed on top of a chip on board (COB).

Figure 5:
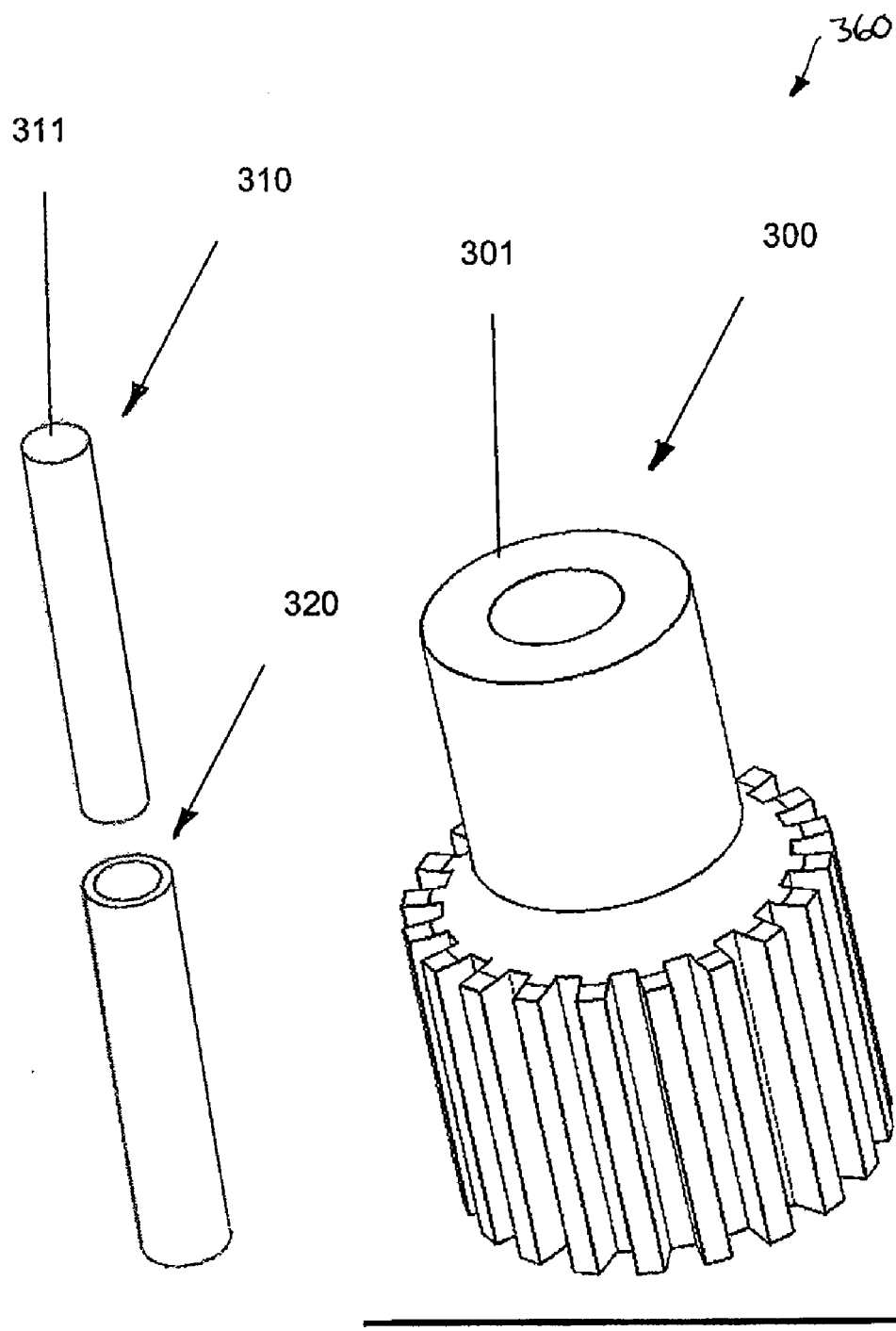
FIG. 5 is an isometric view of another exemplary embodiment of a LED retrofit light source in which a remote phosphor conversion layer is located on top of a chip on board (COB), the light source being in a partially unassembled configuration, including a heat sink body, an inner rod, and an outer tube.

Referring to FIG. 5, a light source 360 is shown in isometric view and includes an outer heat sink body 300, an inner rod 310, and an outer tube 320. In the illustrated embodiment, the outer tube 320 is a polycrystalline alumina/aluminum-oxynitride tube (PCA/AlON) tube. The heat sink 300 can be constructed out of a material having high thermal conductance such as aluminum or copper. The heat sink 300 can be plated with a material such as a gold or silver. Other materials having similar properties can also be used, including in place of, in conjunction with, or as a coating. Alternatively, the heat sink can be made of a polymer, such as a plastic, which can help make the cost of manufacturing inexpensive. A top face 301 of the heat sink 300 can be wire bonded to the heat sink 300, and in such instances, a coating that is compatible with such wire bonding can also be included. Examples of such coatings include, but are not limited to, a coating including gold, silver, or zinc. Additionally, coating the heat sink 300 can protect against corrosion. Further, coating the heat sink 300 can allow for a desirable thermal interface between the light source 360 and an inside of an otoscope in which it will be installed, as illustrated, for example, in FIG. 14, in which the light source 360 is incorporated into the otoscope 500.

The inner rod 310 can be used for electrical and thermal conductance. The inner rod 310 can constructed out of a material with high thermal conductance, such as metal, including metals like aluminum or copper. Any other number of materials that have or can be adapted to have high thermal conductance can also be used. The outer tube 320 can be plated with a material such as gold or silver for the reasons described above, and with other similar materials, as also described above. In exemplary embodiments, the outer tube 320 can be molded or extruded out of PCA and/or AlON, which are both readily available materials. Other materials can also be used to achieve the desired effect. Likewise, an alternative to including the outer tube 320 includes anodizing the inner rod 310. The anodization can be a thermal but not electrical conductor. The outer tube 320 or anodized inner rod 310 can serve as a lateral heat transfer enhancer(s) while providing complete electrical insulation. During assembly, the inner rod 310 can be coupled to the outer tube 320 in any number of ways. For instance, the inner rod 310 can be press-fit inside the outer tube 320 using any number of physical forces. In one exemplary embodiment, the inner rod 310 is press-fit tightly against the outer tube 320 to allow for good thermal transfer therebetween. In some embodiments, an adhesive component can be used between the inner rod 310 and the outer tube 320, such as a thermal epoxy. The thermal epoxy can be applied to the outsides of the inner rod 310 and/or the insides of the outer tube 320 so that air space between the two components can be minimized or eliminated when the inner rod 310 is disposed within the outer tube 320. Alternatively, a sealing substance can be disposed between the inner rod 310 and the outer tube 320 after they are coupled together. A sub-assembly of the inner rod 310 and the outer tube 320 can be coupled to the heat sink 300, for instance by press-fitting the sub-assembly into the heat sink 300 by way of a physical force. The sub-assembly can generally be referred to as a conductive material. The physical force can be applied in any number of ways. For the same reasons just stated, it can be desirable to have close contact between the heat sink 300 and the sub-assembly, and therefore, a thermal epoxy can be used if needed. Further explanation of the orientation and purpose of these features will be described in the description accompanying FIG. 6.

Figure 6:
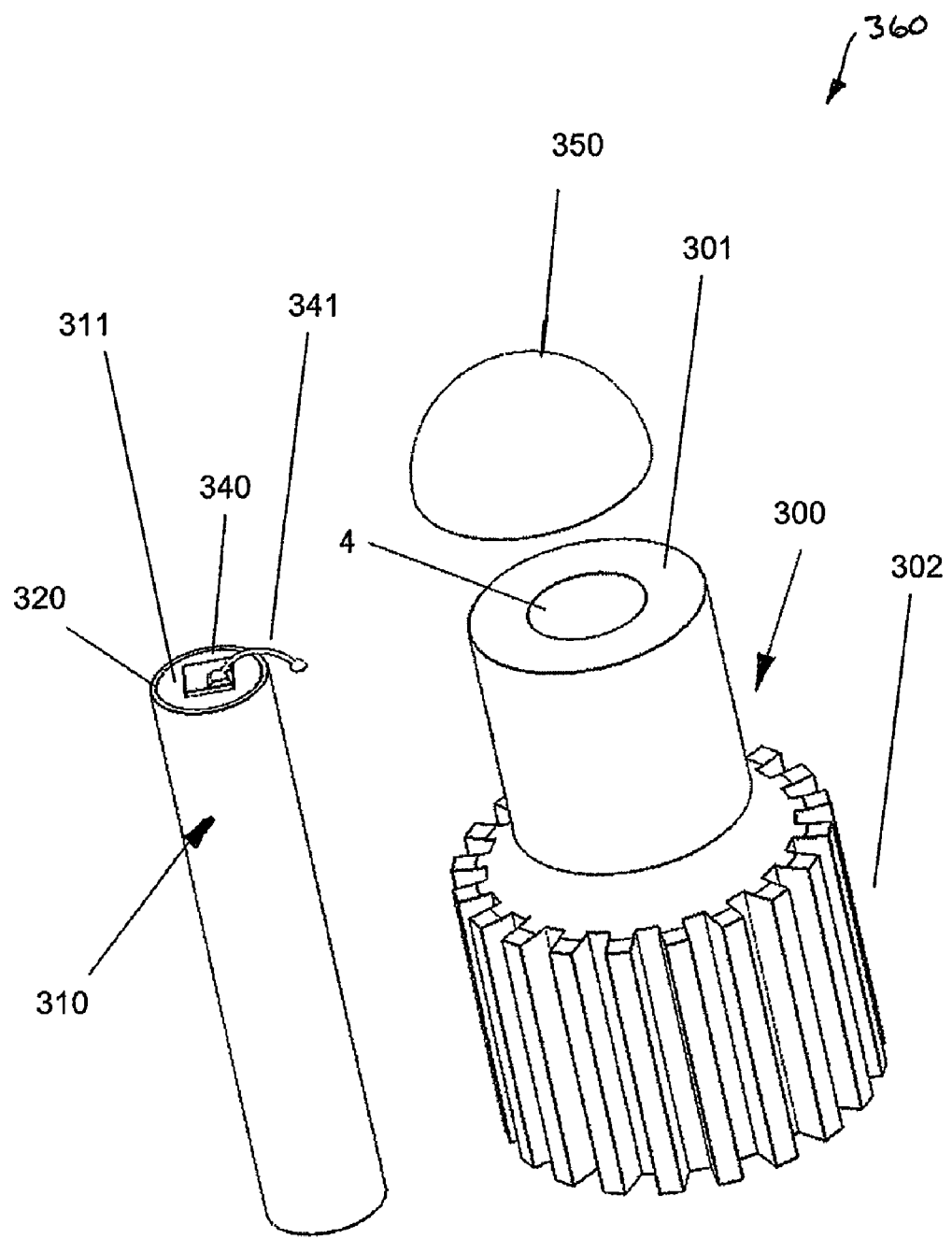
FIG. 6 is an isometric view of the LED retrofit light source of FIG. 5 in another partially unassembled configuration, in which the inner rod is disposed within the outer tube and including a remote phosphor dome separate from the heat sink body.

Referring to FIG. 6, there is shown an isometric view of the light source 360 in a partially un-assembled configuration. In particular, the sub-assembly of the inner rod 310 and the outer tube 320, the heat sink 300, a blue light-emitting die or chip (LED die) 340, a wire bond 341, and a remote phosphor dome 350 are illustrated. Because white light can be favorable for the light source 360, and the surface area for which a white LED package must be mounted is quite small, a COB approach is used to directly integrate the LED with the heat sink. This method can yield excellent heat extraction because the material interfaces between a bottom of the LED die 340 and the heat sink 300 are minimized. This can be achieved by having the LED die 340 mounted on top of the inner rod 310. The LED die 340 can be mounted to the inner rod 310 in any number of ways using any number of substance. For example, the LED die 340 can be bonded at a top surface of the inner rod 310 using epoxy die bonding or eutectic die bonding. The LED die 340 can also have a number of different properties. For instance, in one exemplary embodiment the LED 340 can have peak emissions between approximately 445 nanometers and approximately 475 nanometers. Examples of such dies include dies manufactured by Nichia, OSRAM Opto, and Cree. The LED die 340 can be chosen that has an anode or cathode, depending on the specific device being retrofitted, so that when the inner rod 310 makes contact with the battery electrical contact inside an otoscope or other device, the polarity is correct.

Figure 7:
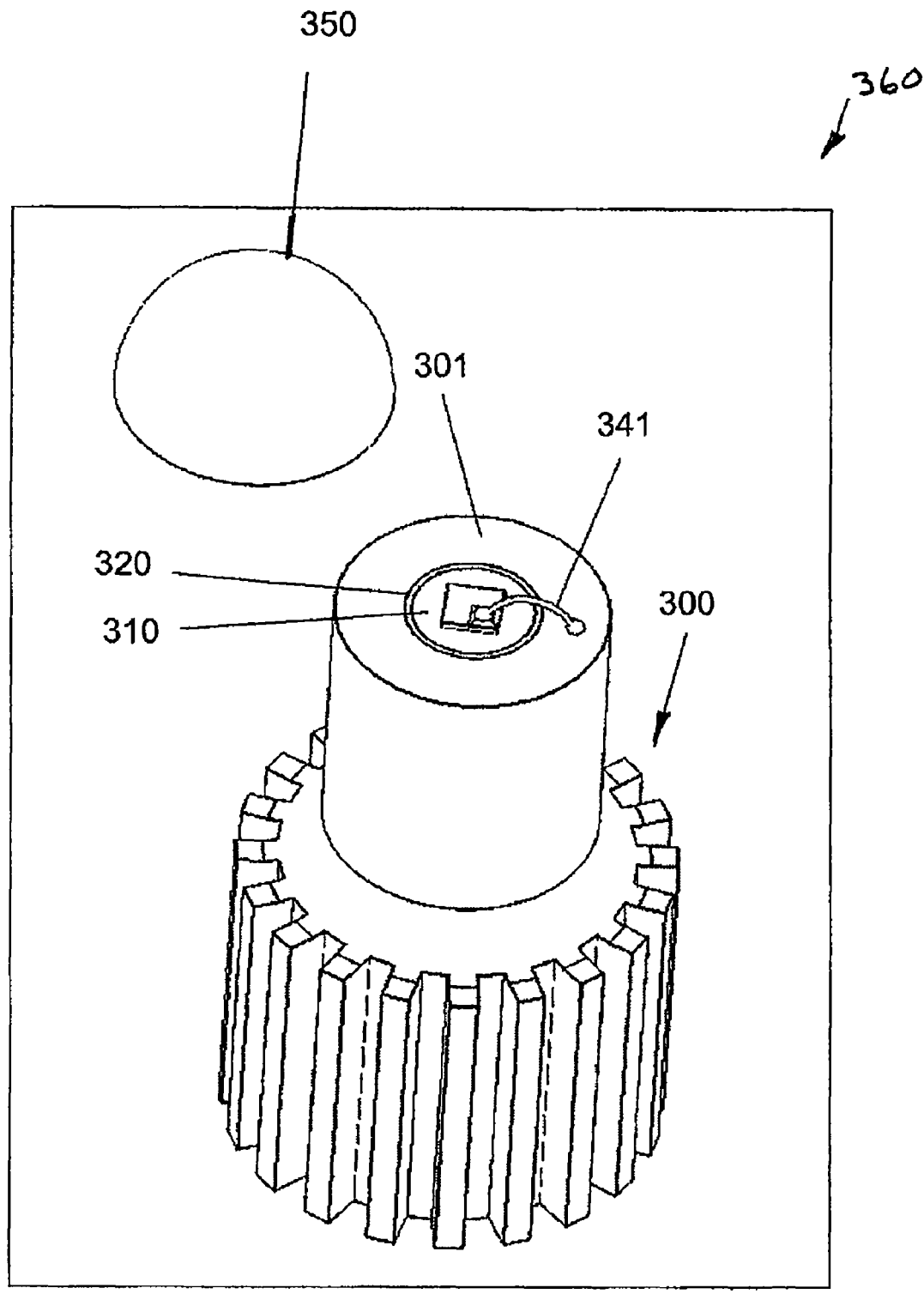
FIG. 7 is an isometric view of the LED retrofit light source of FIG. 6 in a further partially unassembled configuration, including the inner rod and the outer tube being disposed within the heat sink body and the remote phosphor dome still being separate from the heat sink body.

Once the LED die 340 has been bonded to the inner metal rod 310 on a face 311 thereof, an electrical contact can be made between a cathode of the LED die 340 and a cathode of the heat sink 300. The heat sink 300 can serve as both a cathode and a cooling device. For example, in the illustrated embodiment the heat sink 300 includes one or more radiating fins 302 that transfer heat from the LED die 340 to the oto-scope's metal body, thereby resulting in an even greater cooling surface area. The top face 301 of the heat sink 300 can be where electrical contact between the cathode of the LED die 340 and the cathode of the heat sink 300 is made. This electrical contact can be bridged using the wire bond 341. The wire bond 341 can be bonded from the cathode point of the LED die 340 over to the heat sink 300. The heat sink 300 can be compatible with wire bonding, thereby serving as an excellent point of contact for the wire bond 341. One way of achieving the excellent point of contact for the heat sink 300 can be by including a plating made of materials such as gold, silver, or zinc. A better view of the completed wire bond can be seen in FIG. 7. In FIG. 7, the remote phosphor dome 350 can be seen and will be explained in further detail below.

Referring to FIG. 7, there is shown an isometric view of the light source 360 in another partially un-assembled configuration showing the inner rod 310 inserted inside of the outer tube 320 to form a sub-assembly, and the sub-assembly inserted into heat sink 300. The remote phosphor dome 350 is shown as being removed from a top of the heat sink 300, but when coupled together the dome 350 and the heat sink 300 with the sub-assembly disposed therein and the LED die 340 can form the fully assembled light source 360. A portion or the entire surface of any of the LED die 340, the wire bond 341, the inner rod 310, the outer tube 320, and the heat sink 300 can be covered with one or more drops of silicone that can serve as index matching of refraction for the LED to enhance blue light extraction. In one exemplary embodiment, the entire surface of each of the LED die 340, the wire bond 341, the inner rod 310, the outer tube 320, and the heat sink 300 is covered by at least one drop of silicone. The dome 350 can be coupled to the heat sink 300 after the silicone is placed on the various components of the light source 360, and thus can be placed on top of the drop of silicone. The remote phosphor dome 350 can have a number of shapes and sizes, but in the illustrated embodiment the dome is hemispherical is shape to form a shell or dome layer. The phosphor dome 350 can made of clear plastics or silicone blended with a mix of phosphors to convert blue light from the light emitting diode into warm white light, which can have a high color rendering index (CRI), for instance, approximately greater than about 85. The warm color temperature typically required for the scope, which can include a color temperature (CCT) from approximately 2700 K to approximately 3200 K, can be achieved by varying the ratio of commercially available red phosphors and YAG/Ce yellow phosphors manufactured for LED use.

Figure 8:
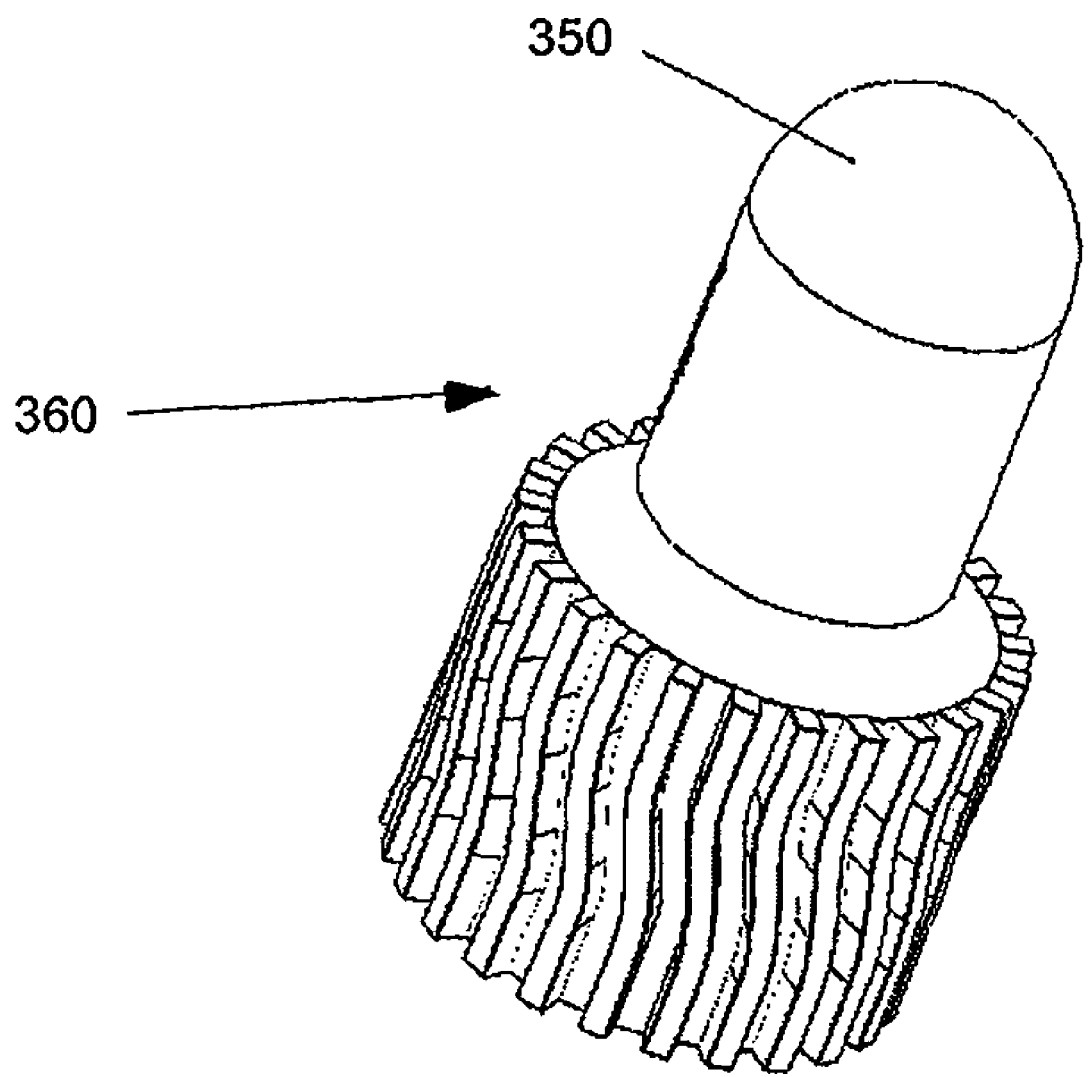
FIG. 8 is an isometric view of the LED retrofit light source of FIG. 7 in an assembled configuration with the remote phosphor dome being coupled to the heat sink body.

Referring to FIG. 8, there is shown an isometric view of the light source 360 in its fully assembled configuration. The remote phosphor dome or shell 350 can be seen installed on top. The dome 350 can be coupled to the heat sink 300 by way of male and female components associated with the dome 350 and the heat sink 300, a snap-fit configuration, an interference-fit configuration, or any number of ways by which two components can be coupled. The completed LED retrofit using COB and remote phosphor can now be seen finished as light source 360. In the illustrated embodiment, the heat sink fins are shown in a spiraled configuration, rather than the straight configuration described with respect to the fins 302 described previously in FIG. 6. The completed LED retrofit lamp or light source 360 can be installed inside an otoscope head, like the head 100 of FIG. 1, replacing a tungsten-halogen bulb 26. It can also be installed in a new otoscope, or other new or existing device.

A second embodiment of a LED lamp emitting white light for the replacement of tungsten-halogen lamps in otoscopes is shown in FIGS. 9-13. This embodiment use the concept of incorporating high-powered white LED packages into a light source. High-powered white LED packages are available off-the-shelf.

Figure 9:
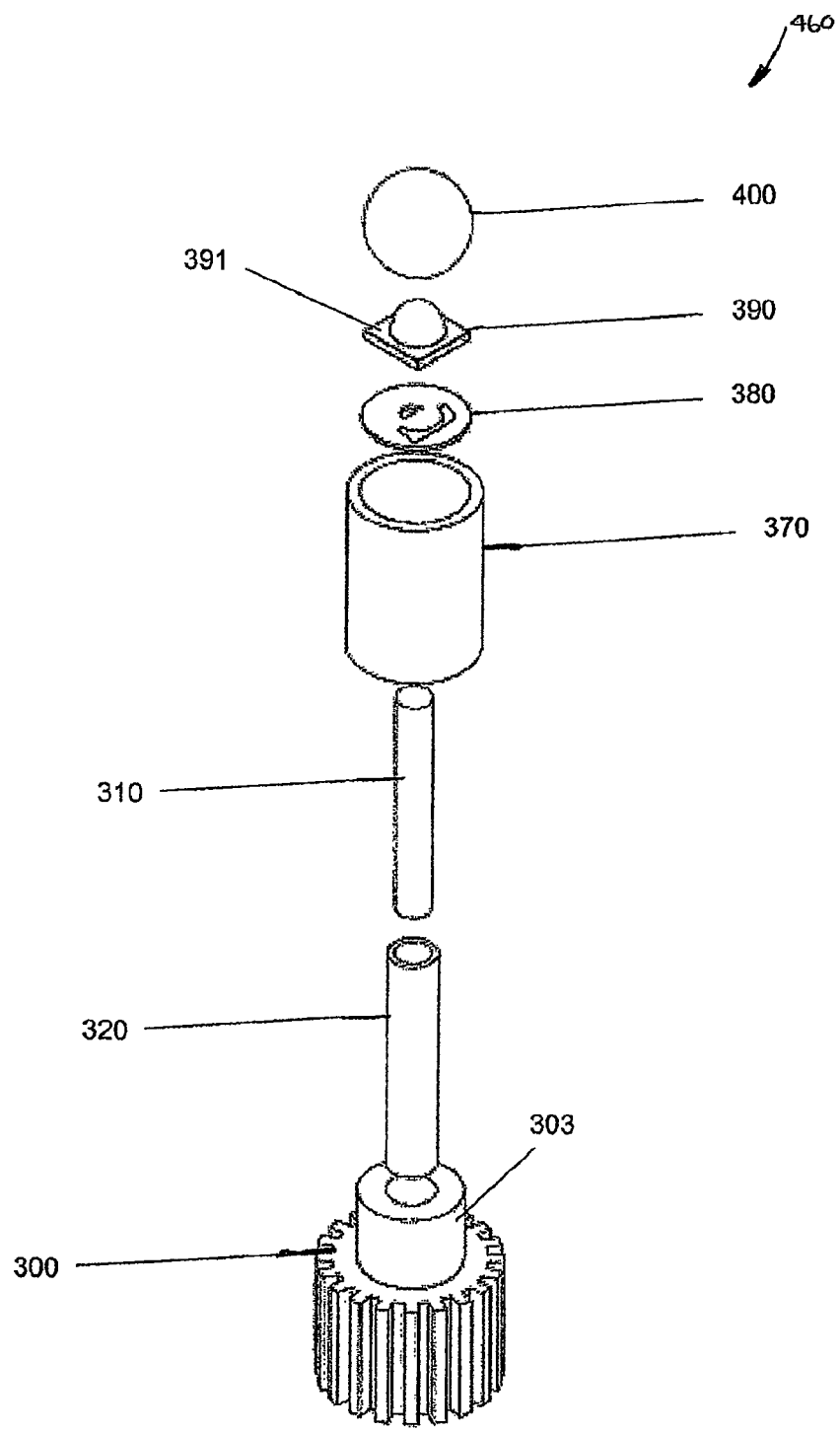
FIG. 9 is an isometric, exploded view of another exemplary embodiment of a LED retrofit light source in which a newly available, off-the-shelf, high-powered white LED package is incorporated therein.

Referring to FIG. 9, there is shown an isometric view of an embodiment of a light source 460 in a fully exploded configuration. This embodiment shares the following same components as the first embodiment of the invention: the heat sink 300, the inner rod 310, and the outer tube 320. Each of these components can have properties similar to those described above for the components. For example, the components can be coated and assembled in a similar manner. The main difference between the light source 460 and the light source 360 is that the light source 460 incorporates a high-powered white LED package 390 into the design. This white LED package is newly available from manufacturers such as Nichia, OSRAM Opto, and Cree. The original technology of creating a white LED package 390 using a blue chip and on-chip phosphor conversion layer is described, for example, in U.S. Pat. Nos. 5,998,925 and 6,069,440 to Shimuzu et al. and assigned to Nichia America, both of which are hereby incorporated by reference in their entireties. In the illustrated embodiment, the white LED package 390 is a Nichia 119. Advancements included in the present invention include a ceramic substrate 391 and new phosphor blends that yield a desirable CCT of approximately 2700 K to approximately 3200 K and a desirable CRI of approximately greater than about 85. These advancements allow for a very high lumen per watt rating, which in turn can yield a high power and light output efficiency. In this embodiment, the white LED package 390 can be mounted on the face 311 of the inner rod 310 and on the heat sink 300. Unlike the light source 360, a wire bond is not used because the white LED package 390 has its anode and cathode connection points at a bottom of the ceramic substrate 391 via gold plated electrically conducted pads.

A spacer 380 can be molded out of a high thermally conductive ceramic material such as PCA and/or AlON, or other high conductance electrically insulated material as desired. The spacer 380 can be placed between the heat sink 300 and the white LED package 390. The material used to form or coat the spacer 380 should be an electric insulator but thermal conductor. The spacer 380, which as shown is a ring shape but can have any number of shapes depending on the other components with which it is used, can be thin to minimize the time it takes for the heat to extract down from the white LED package 390 and into the heat sink 300 and inner rod 310. The integration between the white LED package 390 and the other components of the lamp are described below with respect to FIGS. 10-12.

A sleeve 370 can be designed to fit directly over an upper portion 303 of the heat sink 300. The, the sleeve 370 can be disposed around at least a portion of the heat sink 300 and the sub-assembly formed by the inner rod 310 and the outer tube 320 disposed in the heat sink 300. In the illustrated embodiment the sleeve 370 is tubular. In other embodiments, the heat sink 300 can be configured to have the equivalent of the sleeve 370 integrally formed as part of the heat sink 300. The sleeve 370 can be constructed out of a material with high thermal conductance, such as a metal. Any number of metals can be used, including, for example, aluminum or copper. Alternatively, the sleeve 370 can be plated with a conductive material, such as a metal. Any number of metals can be used as a plating, including, for example, gold or silver. Additionally, coating the sleeve 370 can protect against corrosion. Further, coating the sleeve 370 can allow for a desirable thermal interface between the light source 460 and an inside of an otoscope in which it will be installed.

During assembly, after the white LED package 390 has been mounted, the sleeve 370 can be press-fit onto the upper portion 303 of the heat sink 300, for example, by use of physical force. A number of different manners of exerting a physical force can be used to assemble the sleeve 370 and the heat sink 300. In one exemplary embodiment, the sleeve 370 is press-fit tightly against the upper portion 303 to allow for good thermal transfer therebetween. If desired, a thermal epoxy that is readily available can be applied to the inside walls of the tubular metal sleeve 370 so that it has no air space when pressed onto the upper part 303 of heat sink 300.

In some embodiments, an adhesive component can be used between the sleeve 370 and the upper portion 303, such as a thermal epoxy. The thermal epoxy can be applied to either or both of the conjoining surfaces of the sleeve 370 and the upper portion 303 so that air space between the two components can be minimized or eliminated when the sleeve 370 is coupled to the heat sink 300. Alternatively, a sealing substance can be disposed between the sleeve 370 and the upper portion 303 of the heat sink 300 after they are coupled together.

An optic 400 can be designed for each application to efficiently extract the light from the white LED package 390. This optic 400 can be in the form of many different shapes such as spherical, convex, concave, etc. Additionally, some applications may require no lens at all. In the light source 460, the optic 400 takes the form of a glass or optically clear plastic such as polycarbonate or acrylic. Any number of other materials which have similar properties of glass or optically clear plastic, i.e., that allows light to be emitted through it, can also be used. A diameter of the optic 400 can be closely matched to the inner diameter of sleeve 370.

Figure 10:
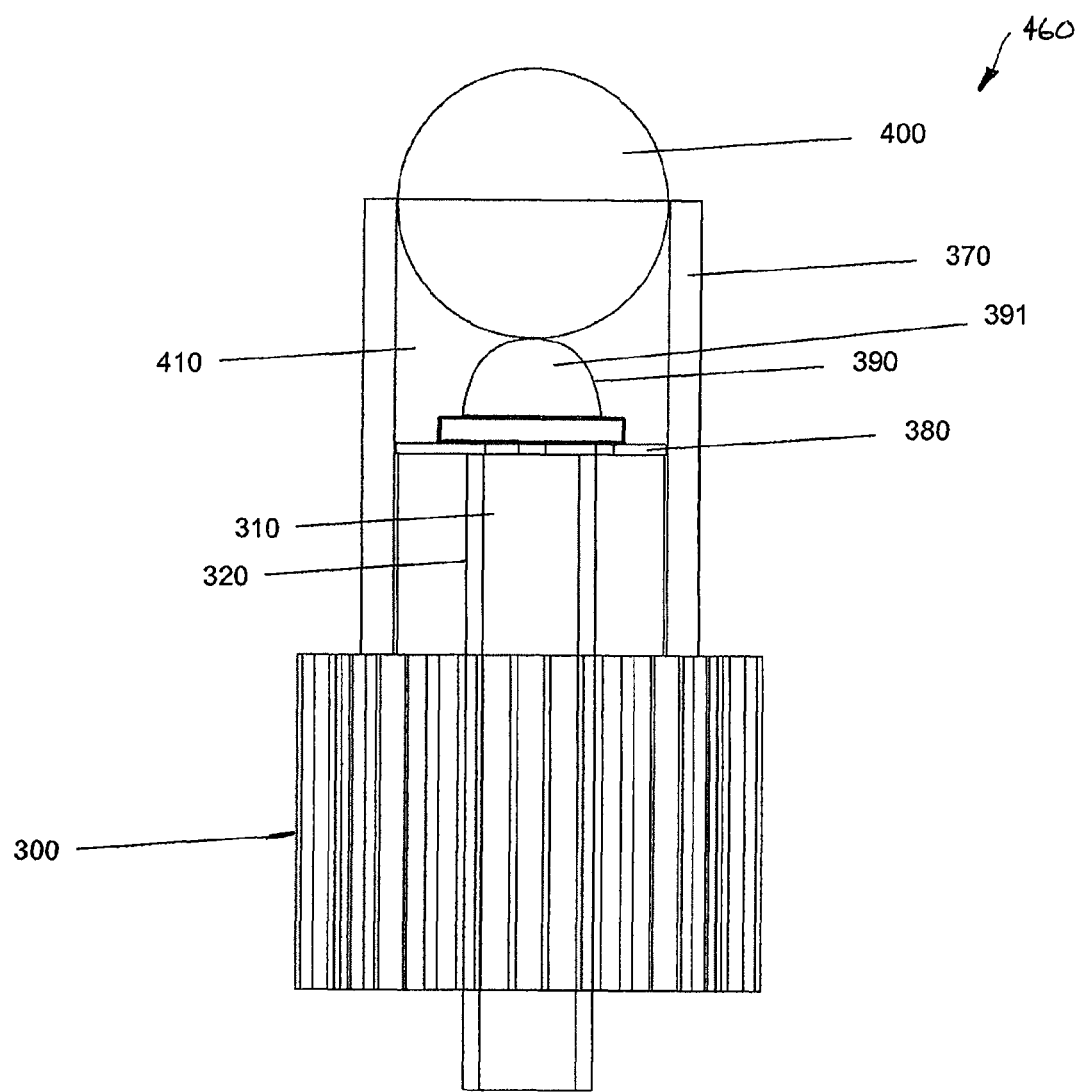
FIG. 10 is a side, view of the LED retrofit light source of FIG. 9 in which a portion of an outer tube of the light source is hidden, the light source including the white LED package, a spacer, and an optic.

Referring to FIG. 10, there is shown a side view of the light source 460. The sleeve 370 has been partially hidden to make to easier to show the assembled state of features such as the white LED package 390, the spacer 380 and the optic 400. As was described in FIG. 9, the spacer 380 can be seated directly under the white LED package 390. During assembly, after the white LED package 390 is located in a desirable position, for instance by soldering the LED package 390 into place as described in greater detail below with respect to FIG. 11, and after the sleeve 370 has been press-fitted into place, an optically clear silicone or optically clear resin can be dispensed into a space 410 surrounding the white LED package 390. This silicone or resin can serve as index matching of refraction for the white LED package 390 and into the optic 400 to enhance white light extraction, similar to the silicone as described with respect to the light source 360. The optic 400 can be directly over the white LED package 390. The silicone or resin filling the space 410 can act as an adhesive to hold the optic 400 permanently into place. Other adhesives or other mechanisms or ways used to couple two components together can also be used. The combination of the optic 400 and the sleeve 370 can work together to extract light from the white LED package 390. This light can then be introduced into an entrance of optical fibers of a device, such as the optical fibers 38 of the otoscope 10 illustrated in FIG. 1. The use of these materials in this order and assembly can create an optical system that results in a high extraction of light into this aforementioned light guide. It would be possible for various other combinations of white LED packages, sizes of tubular metal sleeves, optics, and resins/silicones to be used, depending on the type of miniature bulb the disclosed LED retrofits are designed to feed light into, whether it be an existing device or a newly manufactured device.

Figures 11, 11B:
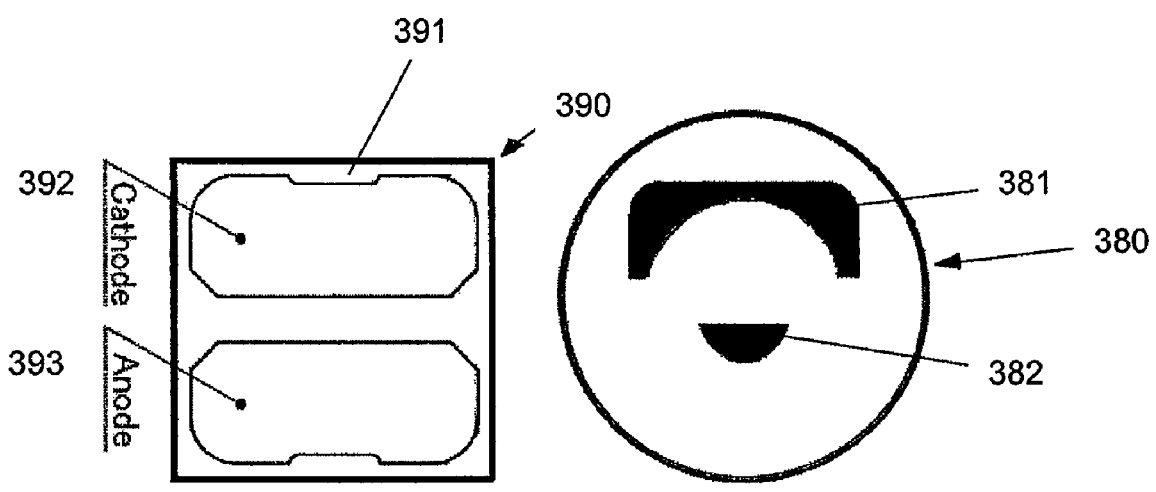
FIG. 11B is partial, top view of the LED retrofit light source of FIG. 10 illustrating a top portion of the spacer.

Referring to FIGS. 11A and 11B, there is shown a top view of the spacer 380 along with a bottom of the white LED package 390. Although many different types of white LED packages can be used in this invention, in the illustrated embodiment a Nichia 119 white LED package 390 is used because of its small overall dimensions, and further, because of the alignment and size of gold plated electrical contact pads 392 and 393. The bottom of the white LED package 390 is shown, and the ceramic substrate 391 is visible as well. The cathode pad 392 provides electrical and thermal interface for the LED. The anode pad 393 provides electrical and thermal interface for the LED as well. In the illustrated embodiment, the spacer 380 has its material shown in white and its voids shown in black. The two voids represent the area in which when the white LED package 390 is placed on top of the spacer 380, the cathode and anodes of the white LED package 390 will be aligned with the cathode and anode voids of spacer 380, as described more in detail in FIG. 12.

Figure 12:
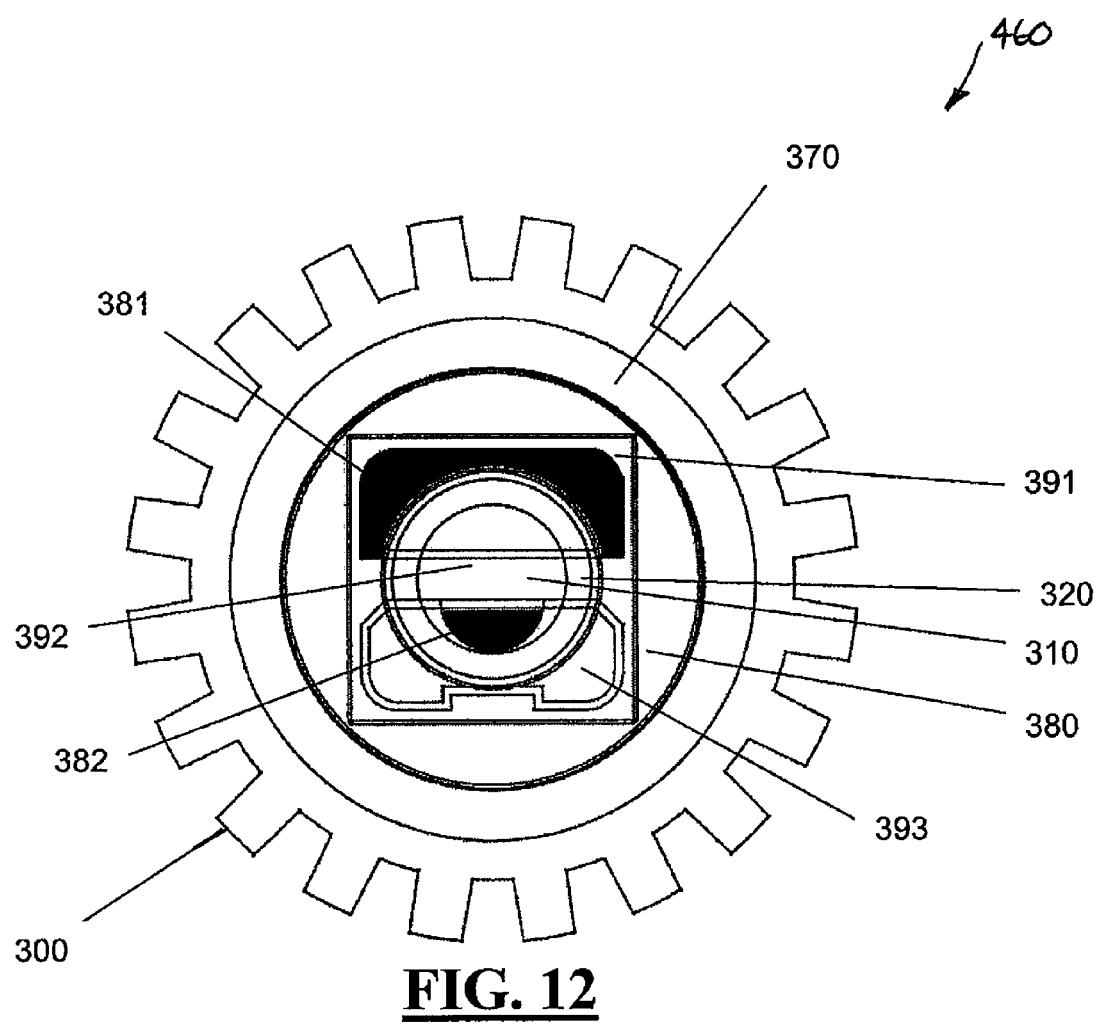
FIG. 12 is partial, top view of the LED retrofit light source of FIG. 10 illustrating the bottom portion of the white LED package and the top portion of the spacer, with the white LED package and the spacer being mounted in a heat sink body, which can be metal.

Referring to FIG. 12, there is shown a top view of the spacer 380 along with the bottom substrate 391 of the white LED package 390 and the top of the heat sink 300. This view is intended to aid in understanding how the spacer 391 integrates with the heat sink 300 and white LED package 390. To ease in the visualizing of this assembly the silicone dome of white LED package 390 has been removed. One exemplary procedure for assembling these components is as follows.

First the heat sink 300, inner rod 310, and outer tube 320 are assembled according to the procedure outlined with regards to the light source 360. Next, the spacer 380 which can be of approximately identical diameter to an outer diameter of the top face 301 of the heat sink 300 can be placed on top of the heat sink 300. Next, commercially available solder paste can be dispensed into the voids 381 and 382 of the spacer 380. The cathode pad 381 and the anode pad 382 of the white LED package 380 are aligned to interface with the cathode void 381 and the anode void 382 on the spacer 380. The entire assembly can then be placed in a heating source, such as a solder reflow oven or hot plate. The solder paste can be cured, thereby making a permanent bond between the white LED package 390 and the heat sink 300 and the inner rod 310. This solder paste can act as both a bonding agent as well as a thermal and electrical transfer agent. The spacer 380 can be effectively "sandwiched" tightly between these aforementioned components, and therefore, can act as a good thermal interface. The cathode pad 381 can now be in contact with the heat sink 300. As a result, when the LED retrofit or light source 460 is inserted into an otoscope or other device, the battery electrical contact inside the otoscope or other device can make contact with the cathode pad 381. The anode pad 381 can now be in contact with the inner rod 310. As a result, when the LED retrofit or light source 460 is inserted into an otoscope or other device, the battery electrical contact inside the otoscope or other device can make contact with the anode pad 381. Consequently, the LED retrofit will illuminate. This method of electrical and thermal contact can be modified for use with different devices so that the polarities are correctly matched between the LED and device. Also of note is that one or more inner rods and tubes can be needed to correctly isolate polarities, depending on device configuration.

Figure 13:
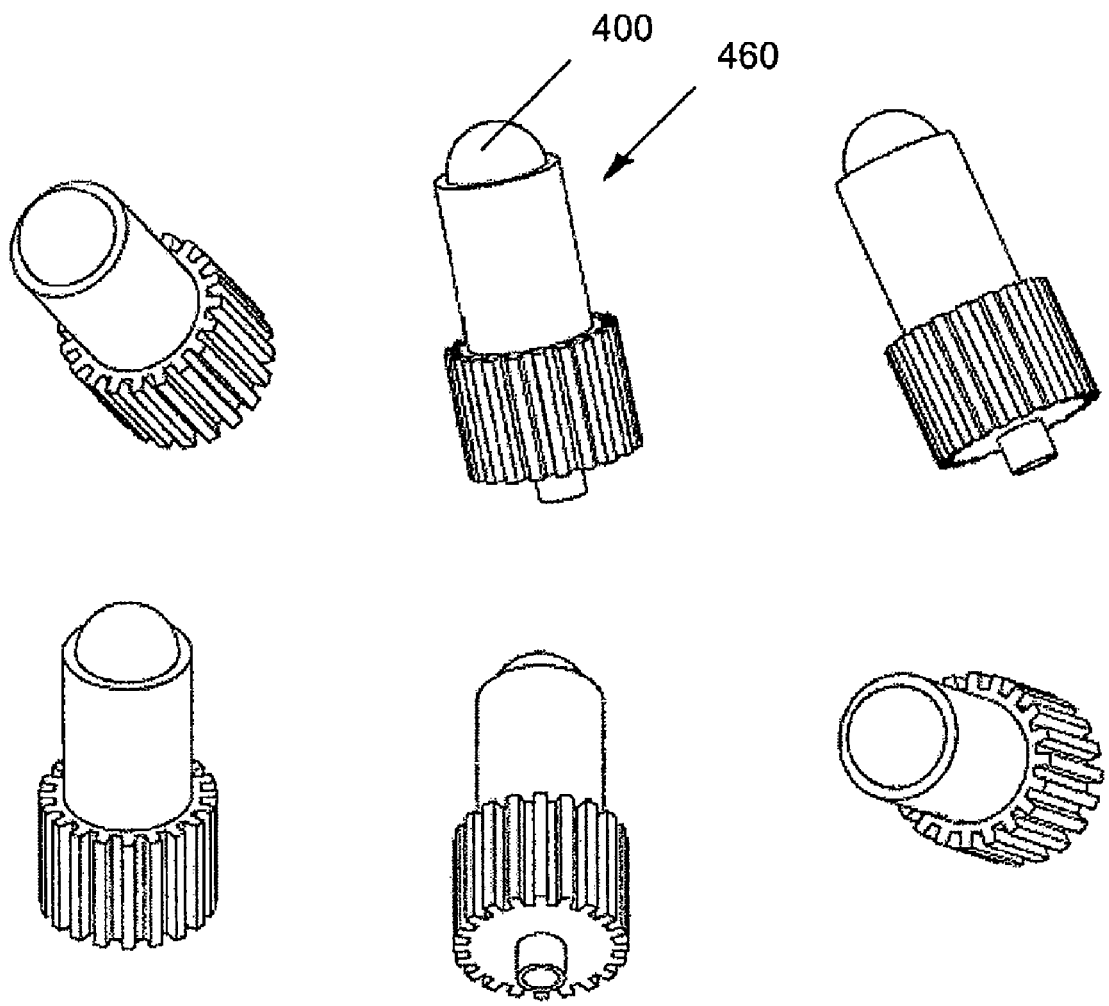
FIG. 13 is various isometric views of the LED retrofit light source of FIG. 10 in an assembled configuration.

Referring to FIG. 13, various isometric views showing various angles of the light source 460 in its fully assembled configuration are illustrated. The optic 400 can be seen installed and sticking out of the top. The completed LED retrofit or light source 460 uses available, off-the-shelf high-powered white LED packages. The completed LED retrofit lamp or light source 460 can be installed inside an otoscope head, like the head 100 of FIG. 1, replacing a tungsten-halogen bulb 26. It can also be installed in a new otoscope, or other new or existing device.

Figure 1:
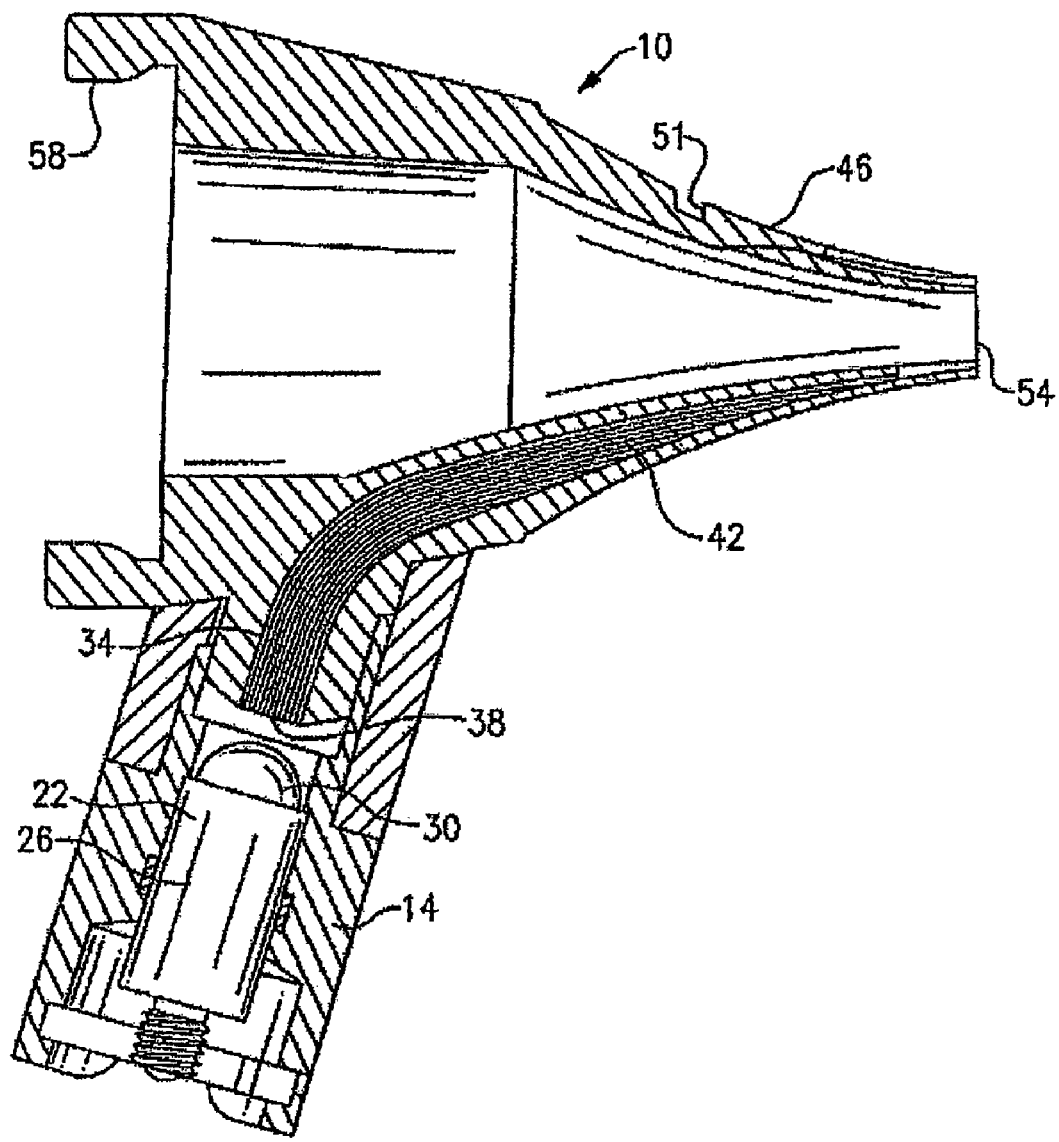
FIG. 1 is a side, cross-sectional view of an otoscope of the prior art.
Figure 2:
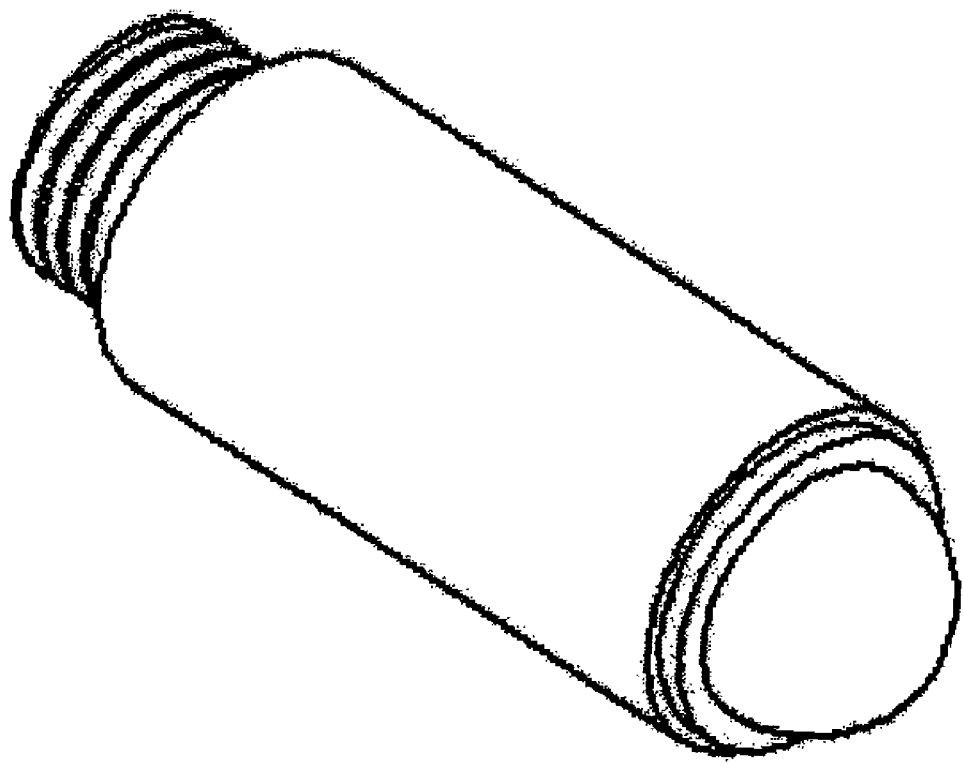
FIG. 2 is an isometric view of a light source of the prior art.
Figure 3:
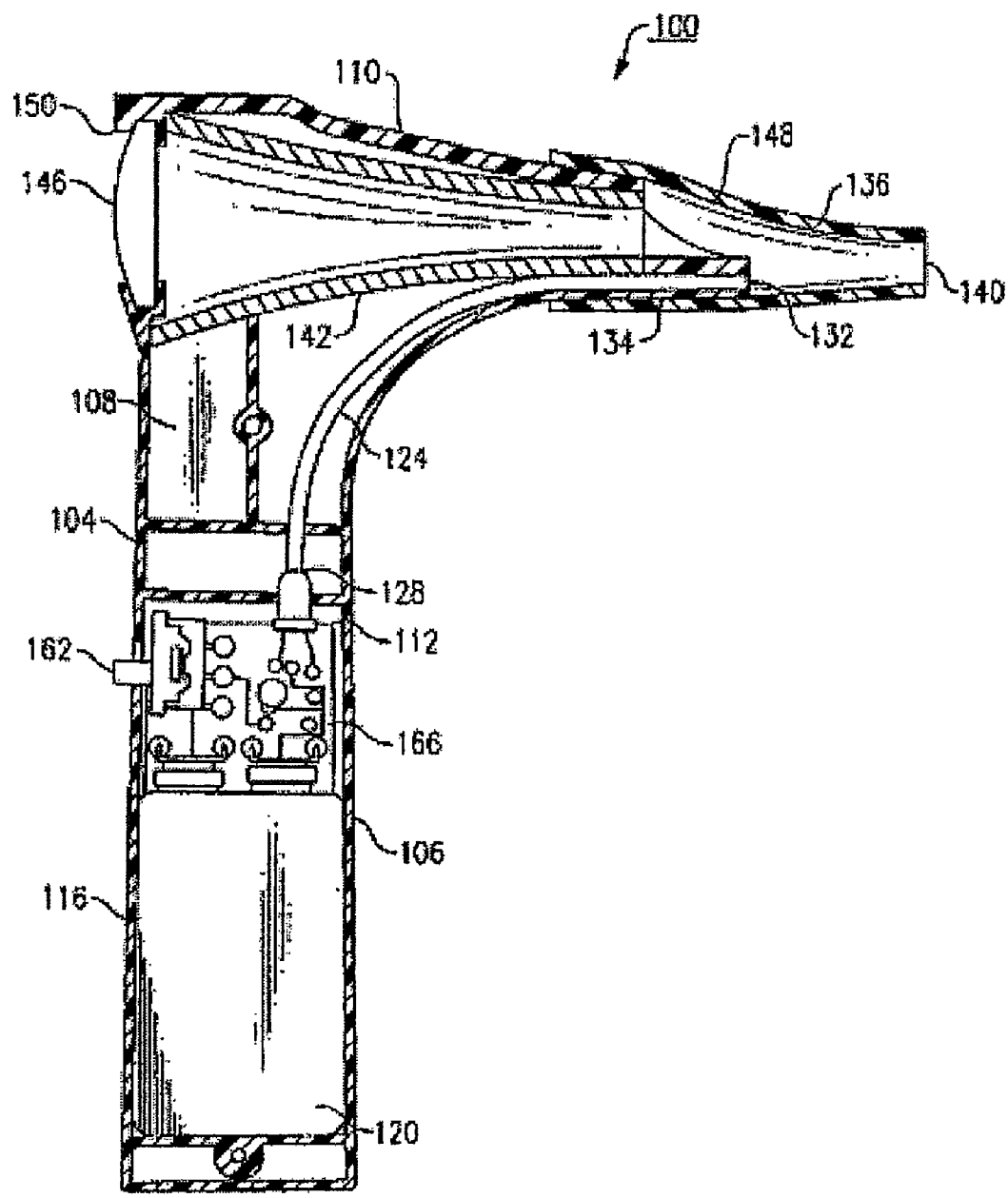
FIG. 3 is a side, cross-sectional view of another otoscope of the prior art.
Figure 4:
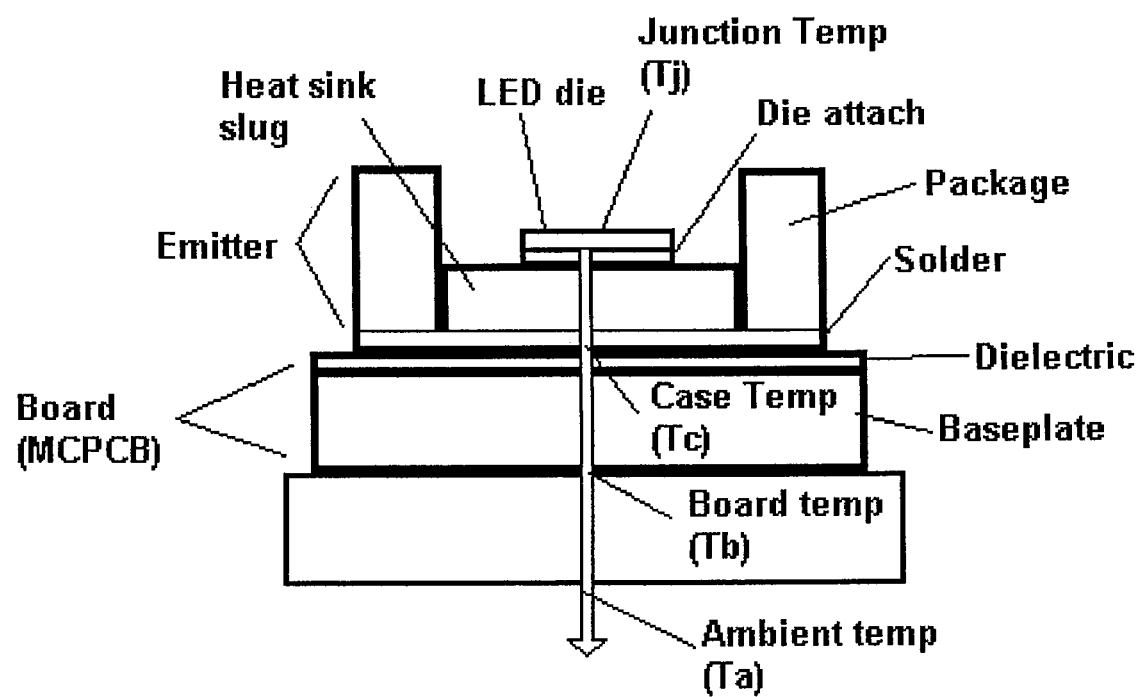
FIG. 4 is a side, schematic view of one exemplary embodiment of a LED retrofit light source in which a remote phosphor conversion layer is located on top of a chip on board (COB) and illustrating a junction temperature, which is denoted as $T_j$.
Figure 14:
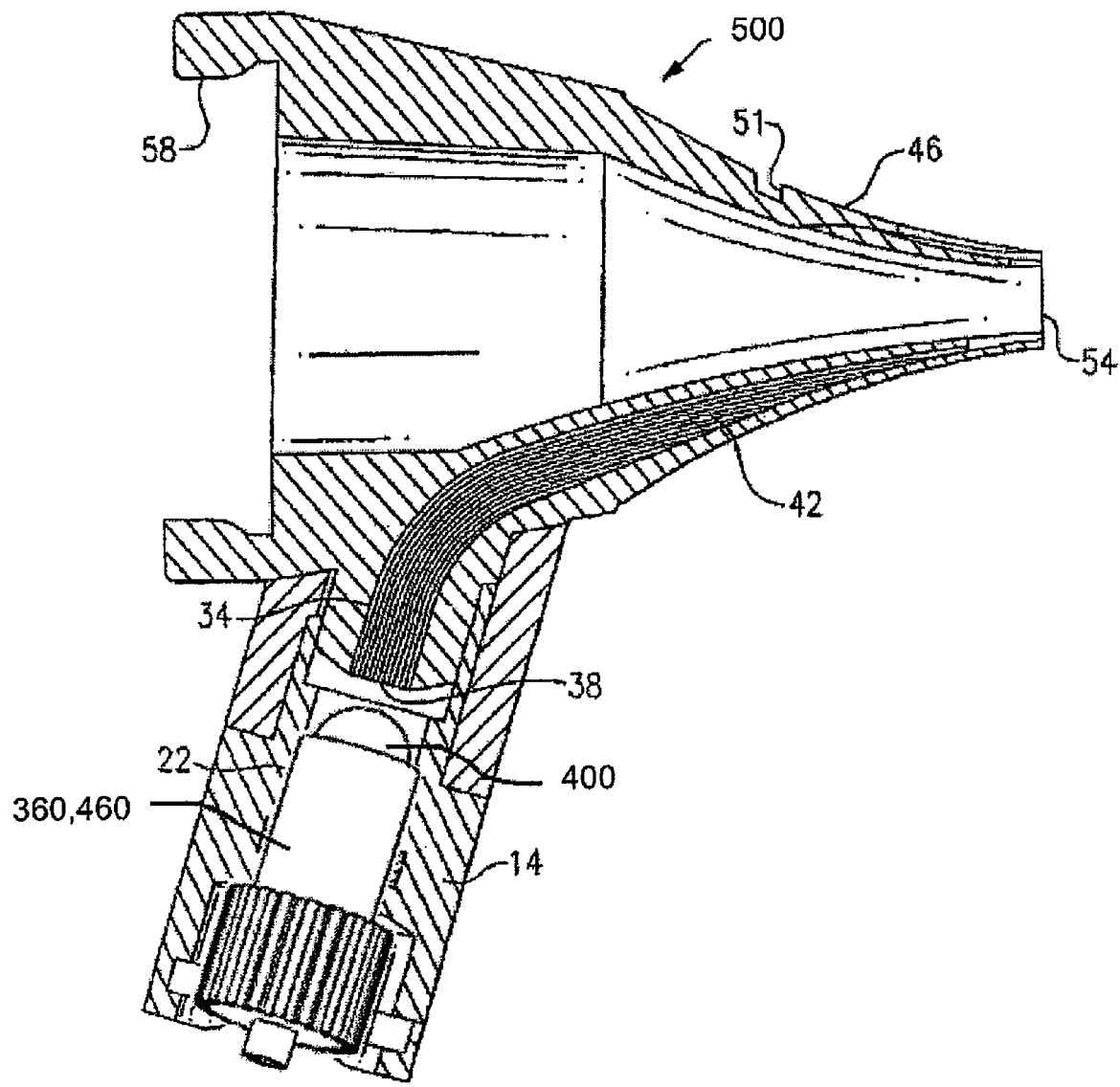
FIG. 14 is a side, cross-sectional view of an otoscope having the LED retrofit light source of FIG. 8 or FIG. 13 installed therein.
Figure 15:
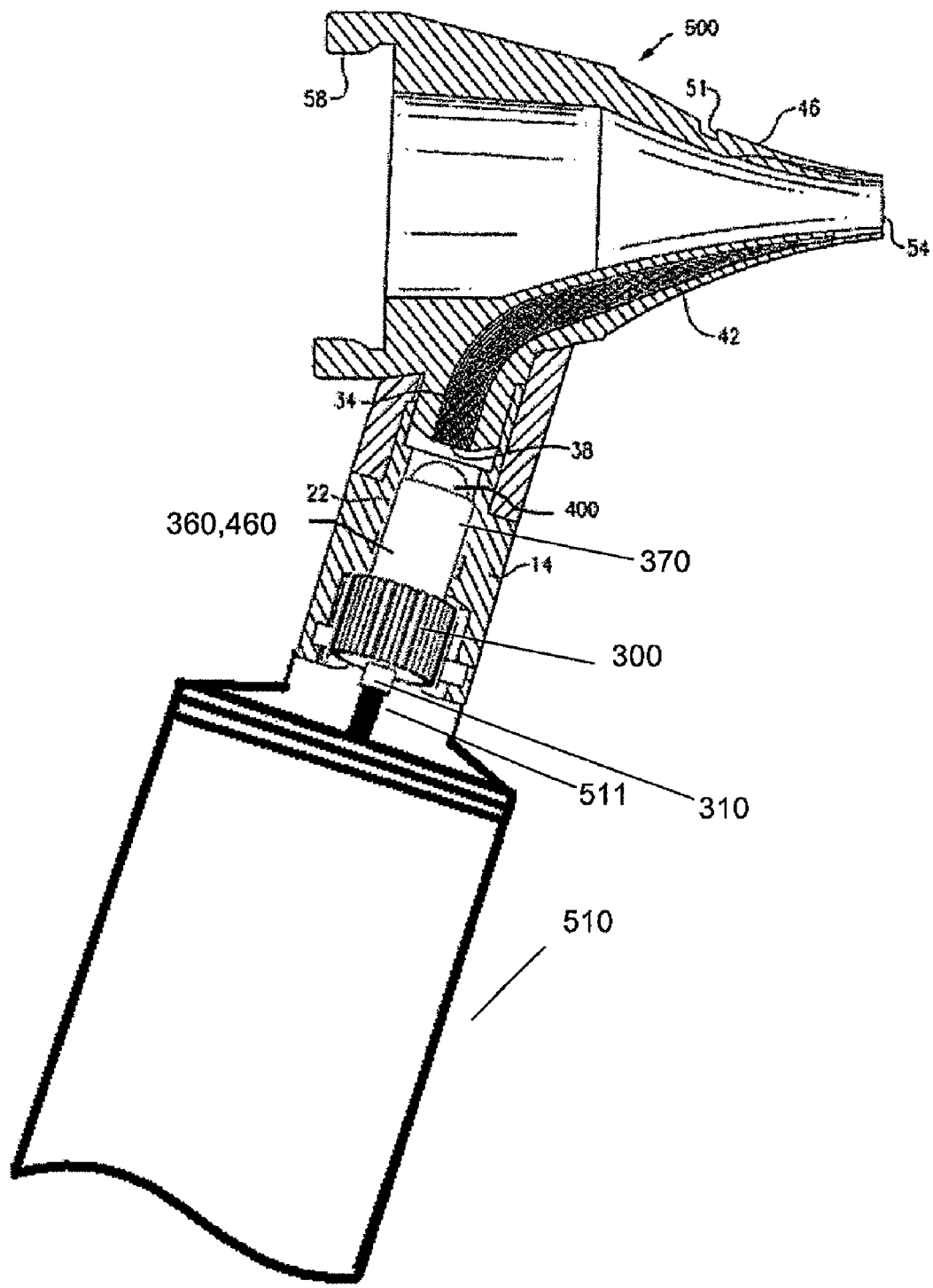
FIG. 15 is a side, cross-sectional view of the otoscope of FIG. 14 connected to an otoscope body.

Referring to FIGS. 14 and 15, there is shown one exemplary embodiment of the light source 360 or the light source 460 being installed in an otoscope 500. To install the light source 360 or the light source 460 into the otoscope 500, the otoscope is dissembled from an otoscope base or body 510. Next, the previous bulb, for example the bulb 26 of FIG. 1, is removed. The light source 360 or the light source 460 is then inserted into the same location. It can be desirable to have the light source 360 or the light source 460 fit tightly into the space previously occupied by the previous bulb to allow for good thermal contact, thereby allowing heat to be extracted away from the light source 360 or the light source 460 to further cool the light source. The otoscope 500 can then be reassembled by connecting the otoscope 500 to the base or body 510 and the otoscope 500 is then ready for use.

The electrical connectivity of the lamp inside of the otoscope 500 is better explained with reference to FIG. 15. The otoscope 500 contains an anode and cathode connection that can be powered by a rechargeable battery or can be plugged into a wall socket. This connection can be brought from the power source and then can be wired to a switch and then to a pin 511 and otoscope body 510. In the illustrated embodiment the otoscope body 510 acts as the cathode and the pin 511 acts as the anode. The LED retrofit light source 360 or the light source 460 has electrical connections as described above and as follows: the cathode connection can be via the entire outer body, the heat sink 300, and the sleeve 370 and the anode connection can be via the inner pin 310. The cathode electrical connection can be made by having the otoscope 500 and the otoscope body 510 make physical contact with the heat sink 300 and the sleeve 370 of the light source 360 or the light source 460. The anode electrical connection can be made by having including a vertical spring pin 511 in the otoscope body. Twisting the otoscope head 500 onto the otoscope body 510 can allow the pin 511 to make physical contact with the pin 310 of the light source 360 or the light source 460. Once the light source 360 or the light source 460 is installed inside the otoscope 500 and the body 510 as described with respect to FIG. 14, the electrical connections are complete and require no additional wiring for on/off operation or dimming operation, which can all be controlled by one or more switches of an otoscope. If the light source 360 or the light source 460 are not designed to have the correct polarities (anode and cathode positions) as these embodiments do, than additional modification, for example wiring, an electronic converter, and/or switching the battery, would be required for proper use of the otoscope. These additional modifications are unfavorable for an easy installation. Further, while in the illustrated embodiments no additional resistance is integrated into the light source 360 or the light source 460 because the voltage rating of the LED associated therewith and the voltage rating of the otoscope 500 are close enough to a match, in other embodiments, additional resistance can be added to the light source 360 or the light source 460, for example, by adding a resistor, resistor wire, or other components that can provide resistance as desired.

A person skilled in the art will recognize that any component of the light sources 360, 460, and the light sources 360, 460 themselves, can be configured to have a variety of shapes, sizes, and configurations depending at least in part on the size of the instrument in which the light sources will be disposed and the shapes, sizes, and configurations of the other components of the light sources. In one exemplary embodiment, the light source has a width in the range of approximately 6 millimeters to approximately 9 millimeters and a length of approximately 15 millimeters to approximately 21 millimeters Likewise, any number of materials can be used to form any of the components of the light sources 360, 460. The materials suggested are merely examples, and other materials having similar properties and characteristics or that are used with light sources, or components in which light sources are used, such as otoscopes. Materials can be adapted to including desirable properties, for instance by coating them or modifying them in other manners. To the extend LED packages are described as having a particular color, e.g., white, a particular range of CCT, e.g., approximately 2700 K to approximately 3200 K, or a particular CRI, e.g., approximately equal to or greater than about 85, a person skilled in the art will recognize that other colors can also be achieved, in conjunction with or in place of white light, a particular CCT, and/or a particular CRI. Further, to the extent manufacturing processes are discussed in a particular order, a person skilled in the art will recognize that other orders can also be used while still keeping within the spirit of the invention.

A number of advantages are realized by the disclosures contained herein. The LED retrofit light sources can be used to replace tungsten-halogen lamps, as well as other lamps, used in commercially available products such as otoscopes. The remote phosphor shell can warm CCT and CRI can be tailored to specific market needs. The light sources of the present disclosure can be at least four times more efficient than tungsten-halogen lamps, as well as other lamps, which in turn can lead to longer life expectancies and shorter battery recharge times. The life-expectancy of the light sources disclosed herein can be approximately 50,000 hours. The light sources disclosed herein can contain no filament, and further, can be unbreakable. In embodiments in which outer shells of the light sources are made of plastic, the plastic remote phosphor shells can be manufactured very inexpensively. In embodiments that incorporate PCA or AlON jackets, such jackets can promote lateral heat transfer enhancement, which in turn can reduce LED temperature as well as provide electrical insulation. In embodiments in which one or more fins are included, the fin(s) can be located in the outer conductor assembly, thereby promoting additional cooling. Use of small, white LED packages in conjunction with spacers made of ceramic or other high conductance, electrically insulating materials can be an excellent way to effective transfer heat into the heat sink, and thus into the otoscope or other device in which the teachings of the present invention are incorporated. Embodiments that use a spacer, or a spacer made of another material but configured to have the same properties of ceramic that are effective for use in conjunction with the teachings herein, is a new way to interface an LED in a small space with a heat sink, and can be an improvement over use of a circuit board material.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A light source, comprising:
    a heat sink having a conductive material disposed therein, the conductive material including an electrically conductive rod disposed in at least a portion of the heat sink;
    a LED die mounted to a top portion of the conductive material and in electrical contact with the heat sink; and
    a phosphor dome coupled to a top face of the heat sink.

2. The light source of claim 1, wherein a life expectancy of the light source is approximately 50,000 hours.

3. The light source of claim 1, further comprising an outer tube disposed around the electrically conductive rod.

4. The light source of claim 1, wherein a color rending index is approximately greater than or equal to about 85.

5. The light source of claim 1, wherein a color temperature is approximately in the range of about 2700 K to about 3200 K.

6. The light source of claim 1, wherein the heat sink further comprises one or more radiating fins.

7. The light source of claim 1, further comprising a wire bond configured to create electrical contact between the LED die and the heat sink.

8. The light source of claim 1, further comprising silicone disposed on at least a portion of at least one of the heat sink, the LED die, and the phosphor dome.

9. A light source, comprising:
    a heat sink having a conductive material disposed therein;
    a sleeve disposed around at least a portion of the heat sink and the conductive material;
    a LED package mounted above the conductive material; and
    an optic located above the LED package and coupled to the sleeve.

10. The light source of claim 9, wherein the heat sink further comprises a polymer.

11. The light source of claim 9, wherein the conductive material further comprises an electrically conductive rod disposed in at least a portion of the heat sink.

12. The light source of claim 11, further comprising an outer tube disposed around the electrically conductive rod.

13. Inc light source of claim 9, further comprising a spacer disposed between the LED package and the conductive material.

14. The light source of claim 9, wherein the LED package comprises a blue chip, an on-chip phosphor conversion layer, and a ceramic substrate.

15. The light source of claim 9, wherein a color rending index is approximately greater than or equal to about 85.

16. The light source of claim 9, wherein a color temperature is approximately in the range of about 2700 K to about 3200 K.

17. The light source of claim 9, wherein the heat sink further comprises one or more radiating fins.

18. The light source of claim 9, further comprising an optically clear substance located in a space surrounding the LED package.

19. The light source of claim 9, wherein a life expectancy of the light source is approximately 50,000 hours.

* * * * *

UNITED STATES PATENT AND TRADEMARK OFFICE
CERTIFICATE OF CORRECTION

PATENT NO.       : 8,106,569 B2
APPLICATION NO.  : 12/778264
DATED            : January 31, 2012
INVENTOR(S)      : David Gershaw It is certified that error appears in the above-identified patent and that said Letters Patent is hereby corrected as shown below:

In the Claims:

Claim 13, column 14, line 48, replace the word "Inc" with the word -- The --.

Signed and Sealed this
Eleventh Day of December, 2012

David J. Kappos
*Director of the United States Patent and Trademark Office*